United States Patent [19]
Redenbaugh et al.

[11] Patent Number: 4,715,143
[45] Date of Patent: * Dec. 29, 1987

[54] ARTIFICIAL SEED COAT FOR BOTANIC SEED ANALOGS

[75] Inventors: M. Keith Redenbaugh, Davis; Zoila Reyes, Menlo Park, both of Calif.

[73] Assignee: Plant Genetics, Inc., Davis, Calif.

[*] Notice: The portion of the term of this patent subsequent to Jan. 7, 2003 has been disclaimed.

[21] Appl. No.: 794,626

[22] Filed: Apr. 24, 1986

Related U.S. Application Data

[63] Continuation of Ser. No. 570,611, Jan. 13, 1984, abandoned, which is a continuation-in-part of Ser. No. 545,678, Oct. 25, 1983, Pat. No. 4,583,320, which is a continuation-in-part of Ser. No. 433,688, Oct. 12, 1982, Pat. No. 4,562,663.

[51] Int. Cl.$^4$ ............................ A01C 1/06; A01G 9/10
[52] U.S. Cl. ............................................. 47/57.6; 47/58
[58] Field of Search ................... 47/57.6, DIG. 9, 58; 111/DIG. 1; 435/177–180

[56] References Cited

U.S. PATENT DOCUMENTS

| | | | |
|---|---|---|---|
| 2,967,376 | 1/1961 | Scott | 47/57.6 |
| 3,600,830 | 8/1971 | Hamrin | 47/57.6 |
| 3,688,437 | 9/1972 | Hamrin | 47/57.6 |
| 3,734,987 | 5/1973 | Hamrin | 47/57.6 |
| 3,973,355 | 8/1976 | McKenzie | 47/57.6 |
| 4,249,343 | 2/1981 | Dannelly | 47/57.6 |
| 4,251,952 | 2/1981 | Porter et al. | 47/57.6 |
| 4,352,883 | 10/1982 | Lim . | |
| 4,534,781 | 8/1985 | Wu et al. | 47/57.6 |

Primary Examiner—Robert E. Bagwill
Assistant Examiner—Danton D. DeMille
Attorney, Agent, or Firm—Limbach, Limbach & Sutton

[57] ABSTRACT

Methods and materials are provided for coating hydrogel capsules which contain encapsulated meristematic tissue substantially free of intact seed coat with a membrane which controls the migration of solvents and their included solutes between the capsule and its environment, thereby creating an analog to natural botanic seed having an artificial seed coat which provides the benefits of natural seed coat. The membranes may be formed of a single compound or various compounds which provide control over the migration of distinct elements.

14 Claims, No Drawings

ARTIFICIAL SEED COAT FOR BOTANIC SEED ANALOGS

RELATED APPLICATION DATA

This application is a continuation of copending application Ser. No. 570,611, filed Jan. 13, 1984, now abandoned, which is a continuation-in-part of copending application Ser. No. 545,678, filed Oct. 25, 1983, now U.S. Pat. No. 4,583,320 which is a continuation-in-part of copending application Ser. No. 433,688, filed Oct. 12, 1982, now U.S. Pat. No. 562,663.

TECHNICAL FIELD

This invention relates to the production of membranes for coating hydrogel capsules, and more particularly to membranes which control solute and solvent migration between the capsule and its environment.

BACKGROUND OF THE INVENTION

A conventional technique of coating hydrogel capsules is to construct a polylysine membrane around the capsule. See F. Lim, U.S. Pat. No. 4,352,883. Other techniques involve methylcellulose compounds, polyvinyl alcohols, plastics, and other compounds. See L. Lachman, H. A. Lieberman and J. L. Kanig, eds. "The Theory and Practice of Industrial Pharmacy," Lea and Febiger, Philadelphia, PA, 1970, p. 197-225.

However, conventional membranes do not control the passage of solvents, particularly water. An additional drawback is the failure to control the passage of small molecular weight solutes across the membrane, unless the membrane is rigid and virtually impermeable.

The above limitations are important when the capsule to be coated is a hydrogel capsule intended to contain living material, notably botanic tissue, such as seeds, somatic embryos and other meristematic tissue. In these applications the membrane must allow respiration by the tissue contained in the capsule, thus an impermeable capsule is undesirable. Yet it is important that the capsule retains sufficient moisture and solutes for tissue viability. Furthermore, the capsule and membrane are often desirably a temporary container for encapsulated tissue, and they will deteriorate or fracture at the desired time for emergence of the tissue, such as e.g. germination.

In addition to the above limitations with available capsule coatings, in some applications it is desirable to provide a coated capsule which is not cohesive or adhesive, as this facilitates handling and bulk storage.

DISCLOSURE OF THE INVENTION

Thus, an object of this invention is to provide methods and compositions which control the passage of solvents between hydrogel capsules and their environment.

Another object of the invention is to provide methods and compositions whereby the passage of solutes into and out of hydrogel capsules is controlled.

Yet another object of the invention is to provide coatings around hydrated capsules which will break down under septic conditions.

A further object of this invention is to provide hydrogel capsules which can be handled as flowable, non-adherent units.

An additional object of the invention is to provide a method whereby coated hydrogel capsules can be stored for an extended time period without substantial water loss from the capsule.

In accordance with the invention, improved methods and membranes are provided for coating hydrogel capsules used for encapsulating material. One aspect of the invention provides a method for encapsulating material and separating the material from its environment comprising encapsulating the material in a hydrogel capsule and surrounding the capsule with at least one membrane which controls the migration of solutes or solvents between the capsule and the environment.

Another aspect of the invention provides a capsule membrane which comprises at least one coating surrounding the capsule which reduces the flow of solvents or solutes between the capsule and its environment.

BEST MODE FOR CARRYING OUT THE INVENTION

Briefly, in accordance with the invention, hydrogel capsules are produced with controlled-release membranes by coating the capsules with specific polymers, binders and solvents.

The invention provides specific polymers and other compounds which are hydrophobic and therefore prevent passage of water when the compounds are formulated as sheets or films. By controlling the passage of water, the present invention also controls the passage of aqueous solutes.

The hydrophobic membranes provided will individualize the capsules and minimize capsules adhesions.

Desirably, in accordance with the invention, the coating can break down at an appropriate point in time to release the capsule contents. The invention is particularly advantageous in creating a protective, solvent-controlling, controlled-release membrane around hydrogel capsules.

Selection of Hydrogels

Individual capsule particles may be produced from a wide variety of hydrogel polymers. Such gels in an uncoated state should allow acceptance, containment and release of specific solvents, solutes and other adjuvants as well as diffusion of gases. The gel should provide an environment strong enough to resist external abrasion and adverse forces, yet pliable enough to allow release of internal components and breakdown to the hydrogel at the appropriate time. It may be desirable to use various gels in combination, either as a mixture, as layers or as discrete regions to achieve the desired results.

Hydrogel capsules made from sodium alginate complexed with calcium contain approximately 90% water. When stored, the water gradually evaporates because calcium alginate is permeable to water. When stored under refrigeration, this water collects in the container, causing the capsules to adhere to the container and each other.

Gels which have been found useful for encapsulating solvents, solutes and other adjuvants include sodium alginate, guar gum, carrageenan with locust bean gum, sodium alginate with gelatin, carboxymethylcellulose, gum tragacanth, sodium pectate and vinyl acetate. Other suitable gels include, but are not limited to:

TABLE 1
Gel Agents

I. Natural Polymers
  A. Ionic bonds (requires complexing agents)
    Alginate with Gelatin
    Sodium Pectate
    Furcellaran
    Pectin
    Hypnean
    Dextran
    Tamarind
    Guar Gum
  B. Hydrophobic Interactions
    Amylose
    Agar
    Agarose
    Agar with Gelatin
    Gelatin
    Starch
    Amylopectin
    Cornhull Gum
    Starch Arabogalactan
    Gum Ghatti
    Gum Karagan
    Ti Gum
    Gum Tragacanth
    Wheat Gum
    Chitin
    Dextrin II. Chemically Modified Natural Polymers
  A. Ionic bonds (requires a complexing agent)
    Ethyl Succinylated Cellulose
    Succinylated Zein
    Carboxymethylcellulose
  B. Hydrophobic Interactions
    Methylcellulose
    Hydroxyethyl Cellulose
  C. Covalent Bonds
    Gelatin with Glutaraldehyde III. Synthetic Polymers
  A. Covalent Bonds
    Polyacrylamide
  B. Hydrophobic Interactions
    Polyethylene Glycol
    Polyvinylpyrrolidone
    Polyoxyethylene
    Hydrophilic Urethane
    Polyvinylacetate
    Vinyl Resins
    Hydron (hydroxyethylmethacrylate) 2-methyl-5-vinylpyridinemethylacrylate-methacrylic acid
  C. Ionic Bonds
    Sodium poly (styrene sulfonate) with poly(vinyl methyl pyridinium) chloride
    Sodium poly (styrene sulfonate) with poly (vinyl benzyl trimethyl ammonium) chloride
    Strongly acidic polyanion with strongly basic polycation
    Bordon Poly Co. 2113 ® (vinyl acetate homopolymer) (Bordon Co.)
    Gelvatol ® (polyvinyl alcohol resin)(Monsanto)

IV. Stabilizing Compounds
  A. Trade Names
    Super Slurper ® (USDA, SEA-AR, Nor. Reg. Res. Lab)
    Viterra ® (Union Carbide)
    Laponite ® (Laporte (United States) Inc.)
    Gelrite ® (Kelco)
    SeaKem ® (FMC Corporation)
    SeaPlaque ® (FMC Corporation)
    SeaPrep ® (FMC Corporation)
    IsoGel ® (FMC Corporation)
  B. Organic Compounds
    Methylan Clear Wallpaper Paste
    Lactose
    Wax
    Protein Colloids
  C. Inorganic Compounds
    1. Clay
    2. Compounds which adhere by means of a water-soluble plastic such as methylcel:
      Fly Ash
      Feldspar
      Celrite
      Bentonite
      Vermiculite
      Diatomaceous Earth
      Lime
      Calcium Carbonate
    3. Other
      Calcium Oxide
      Magnesium Carbonate
      Sodium bicarbonate
      Urea

Encapsulation with Selected Gel

Once the gel has been chosen, there are numerous parameters which influence the characteristics previously mentioned.

A sodium alginate solution, for example, will form a gel when a complexing agent is added. Calcium chloride ($CaCl_2$) is generally used, however, lanthanum chloride, ferric chloride, cobaltous chloride, calcium nitrate, calcium hydroxide, superphosphate fertilizer, and many pesticides such as benefin, alachlor and chlorpropham are also acceptable, as are other multivalent cation compounds.

An important factor which influences the choice of gel agent, and other parameters, is the choice of encapsulated material. In general the coated hydrogel capsules of the present invention will find use as delivery systems for, e.g. living material including eukaryotic cells, micro-organisms and botantic tissue such as seeds, somatic embryos and other meristematic tissue capable of developing into an entire plant body. Alternatively, numerous adjuvants may be encapsulated within the capsules of the present invention, either separately or in combination with each other and with encapsulated living material.

A chosen gel will have a range of concentrations usable in working the invention. A concentration should be chosen to optimize ease of handling, gelling time, strength of gel and coating thickness around the encapsulated material. If the gel is too dilute, the encapsulated material can settle during gel formation and produce an uneven encapsulation.

The sodium alginate may be prepared in a concentration of 1 to 10% w(in grams)/v(in milliliters) in water, more usually 2 to 10% and ideally from 3 to 5%.

Specific adjuvants to be encapsulated may be mixed with the sodium alginate at concentrations specific for the application rates of the particular adjuvants. The dispersed adjuvants in gel solution may then be added dropwise to the complexing agent. Alternatively, the gel solution and complexing agent may be mixed by any of numerous techniques known to the art. These may include droplet formation and agent addition as a one step process by a vibrating nozzle which ejects a gel droplet from one source and coats the droplet with complexing agent from another.

The calcium chloride (or other complexing agent) may be made up in solution at a concentration of 1 to 1,000 millimolar, more usually 20 to 500 millimolar and ideally from 50 to 300 millimolar. Other complexing agents will have different preferred concentration ranges.

The time for gel formation and temperature of the gelling solutions are interrelated parameters, for selected concentrations of gel and complexing agent. The temperature should be chosen in the range of 1° to 50° C., more usually 10° to 40° C., and preferably at 20° to 40° C.

Within the range of acceptable temperatures, a particular value may be chosen to give the shortest possible gelling time consistent with complete gel formation. Typically, the gel will form immediately, but the complexation takes much longer. For a solution of sodium alginate at a concentration of 3.2 grams per 100 milliliters $H_2O$, calcium chloride solution concentration of 50 millimolar, and 25° C. reaction temperature, adequate gelling is obtained in 5 to 120 minutes, more often 10 to 90 minutes and is usually sufficiently complete in 30 to 60 minutes. Alternatively, if 300 millimolar calcium chloride is substituted for 50 millimolar calcium chloride, gelation time is decreased to 2-5 minutes.

The gel characteristics described above are modifiable for each gel, but are determined generally by the concentration parameters and chemical properties of the gel.

Coating the Capsules with Solvent/Solute Controlling membrane

Subsequent to capsule formation, it may be desirable to control permeability of the outer surface of the gel matrix. The encapsulated adjuvants can be coated with a membrane resistant to water or solvent movement. The membrane should be semipermeable to impede the release of the capsule contents or impermeable to the contents with release being effected via microbial degradation, temperature or pH changes, or other physical or biological effects. This membrane can also influence the handling properties of the capsules, particularly the flowability of the capsule.

The coating materials selected to provide membranes for hydrogel capsules will ideally produce membranes with these desirable properties:
1. The membrane will be relatively water-impermeable.
2. The membrane will adhere to the hydrogel capsule.
3. The membrane will optionally be biodegradable.
4. The solvent systems (if necessary) and procedures used to apply the membrane will be relatively harmless to the material encapsulated by the hydrogel.

In general, hydrophobic substances can be used as water-impermeable membranes when used separately, as mixtures or when combined with polymeric binders, such as e.g. ethylene-vinyl acetate copolymers, and cellulose derivatives.

For example, various polymers such as Elvax 4260 ® (ethylene vinyl acetate acrylic acid terpolymer, DuPont, Wilmington, DE) will form coatings resistant to water penetration when mixed with stearic acid, cetyl alcohol, cyclohexane and petroleum ether. Capsules are pretreated with a calcium oxide solution and immersed in the polymer solution. In a similar manner other polymers can be used to coat capsules.

A chosen polymer will have a range of concentrations usable in working the invention. A concentration should be chosen to optimize ease of handling, viscosity, solubility and membrane thickness. If the polymer concentration is too low, the membrane will be readily permeable to water. If too thick, the optionally included meristematic tissue may not germinate.

The Elvax 4260 ® may be prepared in a concentration of 1 to 50% w(in grams)/v(in grams) in cyclohexane, more usually 5 to 20% and preferably 8 to 12%. One gram of this Elvax solution is then mixed with stearic acid, cetyl alcohol, and petroleum ether (60°-110° C. boiling point) at concentrations of optionally 0.01 to 5.0 grams, 0.01 to 5.0 grams and 0.1 to 20 grams, respectively, more usually 0.1 to 1.0, 0.1 to 1.0 and 0.5 to 10.0 grams, respectively to produce a polymer solution. Capsules containing various material and adjuvants are pretreated with calcium hydroxide at a concentration of 0.001 to 1.0 grams per gram water, more usually 0.01 to 0.1 grams per gram. The pretreatment solution is applied to the capsules at a concentration of 0.5 to 20.0 grams pretreatment solution per gram capsules, more usually 1 to 10 grams per gram. Following pretreatment, the capsules are immersed and stirred for 1 to 30 minutes, more usually 3 to 10 minutes in the polymer solution at ambient temperature, 20° to 35° C., more usually 25° to 30° C. Subsequently, the capsules are stirred 1 to 30 minutes, more usually 3 to 10 minutes at 0° to 10° C., more usually 3 to 8° C. The capsules are filtered to remove excess polymer solution and then air dried.

As an alternative to the pretreatment protocol, 0.0001 to 1.0 gram each of glucose and glycerol, more usually 0.01 to 0.10 gram each are added to the calcium hydroxide solution before capsules are pretreated.

As an alternative to the polymer solution, Spermaceti Wax Substitute #573 (J. B. Ross Co., Jersey City, N.J.) can be added to the Elvax 4260 ® solution at a concentration of 0.001 to 2.0 gram per gram Elvax 4260 ® solution, more usually 0.01 to 1.0 gram per gram.

As a further alternative, the polymer solution may be replaced with a solution of 0.05 to 10.0 grams, more usually 0.5 to 5.0 grams of a 1 to 20%, more usually 5 to 15% Elvax 310 ® (ethylene vinyl acetate copolymer) in high boiling point petroleum ether mixed with 0.001 to 2.0 grams each of stearic acid and cetyl alcohol, more usually 0.01 to 1.0 grams each.

As another alternative, the polymer solution may be replaced with 0.01 to 10.0 grams, more usually 0.1 to 5.0 grams of 0.50 to 10%, more usually 1 to 5% aluminum monostearate in toluene mixed with 0.001 to 0.10 grams, more usually 0.01 to 0.10 grams stearic acid. After applying this coating, a second coating may be applied consisting of 0.01 to 10.0 grams, more usually 0.1 to 5.0 grams of 0.5 to 10%, more usually 1 to 5% aluminum tristearate in toluene mixed with 0.1 to 5.0 grams, more usually 0.10 to 1.0 grams of 0.50 to 20%, more usually 5 to 15% Elvax 4260 ® in cyclohexane.

As yet another alternative, the polymer solution may be replaced with 0.10 to 10 grams, more usually 0.50 to 2.0 grams of methylvinyl ether/maleic anhydride copolymer, high molecular weight, dissolved in 5 to 100 milliliters, more usually 10 to 50 milliliters of anhydrous butanol. One drop of sulfuric acid is added to the mixture. This solution is refluxed for 20 to 30 hours at 100° to 120° C.

As an additional polymer alternative, Gantrez ES-435 ® or ES-425 ® (GAF Corporation) may be used.

Other coating compounds which can be used in the present invention to form membranes include, without limitation:

TABLE 2

Capsule Coating Compounds

I. Enteric Coating
　Methylvinyl ether/maleic anhydride
　Styrene maleic acid copolymer
　Styrene-maleic anhydride copolymer
　Ethylene/maleic anhydride copolymer
II. Hydrophobic Polymers
　Ethylcellulose
　Isopropyl myristate
　Polyvinyl acetate phthalate
　Starch acetate phthalate
　Amylose acetate phthalate
　Cellulose acetate phthalate
　Saran
　Butyl rubber
III. Other Compounds
　Keratin
　Shellac
　Carnuba wax
　Paraffin
　Wax
　Fats
　Lipids
　Triglycerides
　Ethylene vinyl acetate copolymer
　Benzyl cellulose
　Petrolatum As an alternative to immersing the capsules in the polymer solution numerous procedures for applying the coating compound to form a hydrogel capsule membrane were used.

Spraying

For this coating procedure an inlet tube was inserted into the lower side of a stainless steel beaker and the beaker covered with a polypropylene mesh attached to the nozzle of a spray gun. The cover was fastened to the beaker with a rubber band. This apparatus simulates a pan-spray tablet coater. The procedure consisted of the following steps:
1. The capsules were placed in the beaker and the cover attached.
2. The capsules were sprayed with the solution of coating compound and the beaker agitated by hand to ensure uniform spraying.
3. The capsules were dried with pressurized air through the inlet tube, while agitating the beaker by hand.

Steps 2 and 3 were repeated until a suitable coating was applied or the solution was exhausted.

Because it was difficult to maintain adequate agitation during this coating process, a nylon mesh bag was substituted for the beaker. The bag was attached to the nozzle, the capsules were alternately sprayed and dried while frequently shaking the bag to uniformly deposit the coating on the capsules.

Immersion

This procedure consisted of the following steps:
1. The capsules were immersed in the coating compound solution, generally at 30° to 35° C.
2. The mixture was stirred 5 min at room temperature and 5 min in an ice-water bath at 10° C.
3. The capsules, were filtered, rinsed with low-boiling petroleum ether, and dried with pressurized air or nitrogen.

Dipping

This procedure consisted of the following steps:
1. The capsules were placed on a basket or bag. (A basket made of polypropylene mesh was used initially, but a bag made of a nylon mesh was found more convenient because of its flexibility.)
2. The bag with the capsules was dipped into the coating compound solution, and agitated to ensure that all the capsules were coated.
3. The bag was removed from the solution, and allowed to drain on a funnel.
4. The capulses were dried with a gentle flow of pressurized air.
5. Steps 2–4 were repeated three or four times and the capsules dried thoroughly with pressurized air.

Experimental

In order to demonstrate the invention, without implying limitations, the following experiments were carried out with a variety of coatings. All quantities labelled percent (%) are grams per 100 milliliters, unless otherwise indicated.

Example A (Coating Capsules Containing Alfalfa Seeds)

500 alfalfa seeds, Saranac AR Lot #27-07-765 (Whitney Dickenson Seed Growers, Homedale, Idaho), were mixed with 200 milliliters of 3.2% sodium alginate. This solution was added drop-wise into 500 milliliters of 100 millimolar calcium chloride to complex the alginate and form spheroid capsules. 40 grams of the capsules were stirred in 8 grams of lime water (containing .20 grams calcium hydroxide plus 1 gram each of glucose and glycerol) for one minute. The solution was decanted and the capsules were immersed in a 30° C. polymer solution containing 2 grams stearic acid, 2 grams cetyl alcohol, 10 grams of a 10% solution of Elvax 4260 ® (ethylene vinyl acetate acrylic acid terpolymer) in cyclohexane, and 40 grams of petroleum ether. The capsules were stirred for 5 minutes at room temperature followed by 5 minutes more in an icewater bath. The capsules were filtered through a nylon cloth, rinsed with 5 milliliters petroleum ether (30°–60° C.), and dried with pressurized air. Subsequent to coating the encapsulated seeds, the alfalfa seeds imbibed water from the alginate capsule, germinated, and emerged from the capsules undamaged.

A.1. As an alternative polymer solution, 40 grams of 2% aluminum monostearate in toluene plus 2 grams stearic acid can be used.

A.2. As another alternative polymer solution, 5.2 grams of spermaceti wax substitute #573, 2 grams cetyl alcohol, 1 gram stearic acid, 10 grams of a 10% solution of Elvax 4260 ® in cyclohexane, and 40 grams of high boiling point petroleum ether can be used.

A.3. As a further alternative polymer solution, 4 grams of stearic acid, 4 grams of cetyl alcohol, and 40 grams of a 10% solution of Elvax 310 ® (ethylene vinyl acetate copolymer) in high boiling point petroleum ether can be used.

A.4. As another alternative polymer solution, 2 grams of stearic acid plus 40 grams of a 2% solution of aluminum monostearate in toluene can be used as a first coating. A second coating can then be applied consisting of 32 grams of a 2% solution of aluminum tristearate in toluene mixed with 10 grams of a 10% solution of Elvax 4260 ® in cyclohexane.

A.5. As a still further alternative, 10 grams of methyl-vinyl ether/ maleic anhydride copolymer was refluxed in 50 milliliters of anhydrous butanol for 21 hours at 110° C. Subsequently, one drop of sulfuric acid was added to the solution. The solution was mixed with alginate-encapsulated alfalfa seeds and dropped into water to produce coated capsules.

A.6. As yet another alternative polymer, Gantrez ES-435 ® or ES-425 ® (GAF Corporation) was mixed with alginate beads and dropped into water to form coated capsules.

EXAMPLE B (Coating Capsules Containing Tomato Seeds)

Six hundred tomato seeds, UC-82 (VGY9225, As-grow), were encapsulated in 2% w/v sodium alginate by dropwise complexation in 100 millimolar calcium chloride. Three hundred of these capsules were stirred one minute in 20 grams of a calcium hydroxide solution containing 1 gram of glucose and 2 grams of glycerol. The calcium hydroxide solution was prepared by stirring 1 gram of calcium hydroxide in 100 milliliters of water for 15 minutes and then filtering the solution. The treated capsules were sieved through a nylon screen, patted dry, and dipped 6 times for 1–3 seconds each in the membrane coating solution. The capsules were blow-dried between dippings. The membrane coating solution consisted of the combination of the following 3 solutions: 2 grams Elvax 4260 ® dissolved in 20 grams cyclohexane, 10 grams of spermacetti wax substitute #573 melted with 4 grams cetyl alcohol and 2 grams stearic acid, and 80 grams each of petroleum ether (50°–110° C.) and methylene chloride. Capsules were planted under both greenhouse and field conditions. The membrane coated, encapsulated seeds had a 100% germination frequency in the greenhouse which was equal to the non-coated, encapsulated seeds and non-coated, non-encapsulated seeds. In the field, membrane-coated, encapsulated seeds had germination frequencies equal to non-coated, encapsulated seeds and better than non-coated, non-encapsulated seeds.

B.1. As an alternative to encapsulation, non-encapsulated seeds were coated as described. Germination rates of coated seeds in the greenhouse equaled rates for non-coated seeds.

EXAMPLE C (Coating Capsules Containing Alfalfa Somatic Embryos)

1. Coating By Immersion

Alfalfa somatic embryos were produced as described by K. A. Walker and S. J. Sato (Plant Cell Tissue and Organ Culture 1:109–121, 1981) using a regeneration medium consisting of Shenk and Hildebrandt (SH) medium (R. V. Shenk and A. C. Hildebrandt, Canadian Journal of Botany 50:199–204, 1972), 100 millimolar proline, and 25 millimolar ammonium. The somatic embryos were encapsulated as in Example A. The encapsulated embryos were then pretreated in a calcium hydroxide solution as in Example B followed by coating as in Example A. The coated, encapsulated somatic embryos were placed on one-half strength SH medium and incubated at 27° C. under 16 hour light/8 hour dark conditions. The percent embryo viability, radicle emergence, and shoot/leaf emergence was statistically equal to that for non-coated, non-encapsulated somatic embryos and for non-coated, encapsulated somatic embryos.

1.A. As an alternative, non-encapsulated alfalfa somatic embryos were coated. Percent embryo viability, radicle emergence, and shoot/leaf emergence was statistically equal to that for non-coated somatic embryos.

2. Coating By Dipping

The experimental protocol C.1. was duplicated, substituting a dipping process for the immersion coating method. The encapsulated alfalfa somatic embryos were placed in a nylon bag and dipped three times in the coating solution. The capsules were blow-dried and dipped three more times with a final blow-drying. The percent embryo viability, radicle, emergence, and shoot leaf emergence was statistically equal to that for non-coated, encapsulated somatic embryos.

2.A. As an alternative, non-encapsulated somatic embryos were coated. Percent embryo viability, radicle emergence, and shoot/leaf emergence was statistically equal to that for non-coated somatic embryos.

EXAMPLE D (Capsule Storage)

Capsules without seeds were coated as in protocol A and stored either in an open container or in a sealed vial. Initial water loss from the capsules during the coating process was 10% w/w of water per capsule. Subsequent water loss through the membrane for capsules stored in an open container was 0 over a 3-day period.

B.1. As an alternative, a different sample retained 93% water over a 10-day period.

B.2. As an alternative, a further sample retained 75% water over a 30-day period.

Although the foregoing invention has been described in some detail by way of illustration for purposes of clarity of understanding, it will be understood that numerous modifications may be practiced within the spirit and scope of the appended claims.

We claim:

1. A membrane coated hydrogel capsule encapsulating meristematic tissue and separating said tissue from its environment, which comprises:

a hydrogel capsule which contains encapsulated meristematic tissue substantially free of intact seed coat; and at least one membrane coating surrounding the capsule which reduces the flow of solvents and their included solutes between the capsule and its environment, thereby creating an analog to natural botanic seed having an artificial seed coat which provides the benefits of natural seed coat.

2. A capsule as recited in claim 1 wherein the capsule further comprises a gel matrix comprising at least one agent selected from the group consisting of sodium alginate, guar gum, carrageenan with locust bean gum, sodium alginate with gelatin, carboxymethylcellulose, gum tragacanth, sodium pectate, vinyl acetate, Furcellaran, pectin, hypnean, dextran, tamarind, amylose, agar, agarose, agar with gelatin, starch, amylopectin, cornhull gum, starch arabogalactan, gum ghatti, gum karagan, Ti gum, wheat gum, chitin, dextrin, ethyl succinylated cellulose, succinylated zein, methylcellullose, hydroxyethyl cellulose, gelatin with glutaraldehyde, polyacrylamide, polyethylene glycol, polyvinylpyrrolidone, polyoxyethylene, hydrophillic urethane, polyvinylacetate, vinyl resins, Hydron (hydroxyethylmethacrylate), 2-methyl-5-vinylpyridine-methylacrylate-methylacrylic acid, sodium polystyrene sulfonate with polyvinylmethylpyridinium chloride, sodium polystyrene sulfonate with polyvinylbenzyltrimethylammonium chloride, strongly acidic polyanions with strongly basic polycations, Bordon Poly Co. 2113 ® (vinyl acetate homopolymer), Gelvatol ® (polyvinyl alcohol resin), Super Slurper ®, Viterra ®, Laponite ®, Gelrite ®, SeaKem ®, SeaPlaque ®, Seaprep ®, IsoGel ®, methylan clear wallpaper paste, lactose, wax, clay, fly ash, feldspar, celrite, bentonite, vermiculite, diatomaceous earth, lime, calcium carbonate, calcium oxide, magnesium carbonate, sodium bicarbonate and urea.

3. A capsule membrane as recited in claim 2 wherein the membrane further comprising at least one compound selected from the group consisting of ethylene vinyl acetate acrylic acid terpolymers, ethylene vinyl acetate copolymers, spermaceti, aluminum stearates, methyl vinyl ether/maleic anhydride copolymers, ethyl cellulose, ethylhydroxyethyl cellulose, stearic acid, glyceryl monooleate, cetyl alcohol and calcium stearate.

4. A capsule as recited in claim 1 wherein the membrane further comprising at least one compound selected from the group consisting of ethylene vinyl acetate acrylic acid terpolymers, ethylene vinyl acetate copolymers, spermaceti, aluminum stearates, methyl vinyl ether/maleic anhydride copolymers, ethyl cellulose, ethylhydroxyethyl cellulose, stearic acid, glyceryl monooleate, cetyl alcohol, calcium stearate, methylvinyl ether/maleic anhydride, styrene maleic acid copolymer, styrene maleic anhydride copolymer, ethylene maleic acid copolymer, ethylcellulose, iospropyl myristate, polyvinyl acetate phthalate, starch acetate phthalate, amylose acetate phthalate, cellulose acetate phthalate, saran, butyl rubber, keratin, shellac, carnuba wax, paraffin wax, fats, lipids, triglycerides, benzyl cellulose and petrolatum.

5. A capsule as recited in claim 1 wherein the capsule further comprises a gel matrix comprising at least one agent selected from the group consisting of sodium alginate, guar gum, carrageenan with locust bean gum, sodium alginate with gelatin, carboxymethylcellulose, gum tragacanth, sodium pectate and vinyl acetate.

6. A capsule as recited in claim 1 wherein:
the capsule further comprises a gel matrix comprising at least one agent selected from the group consisting of sodium alginate, guar gum, carrageenan with locust bean gum, sodium alginate with gelatin, carboxymethylcellulose, gum tragacanth, sodium pectate and vinyl acetate; and
the membrane further comprising at least one compound selected from the group consisting of ethylene vinyl acetate acrylic acid terpolymers, ethylene vinyl acetate copolymers, spermaceti, aluminum stearates, methyl vinyl ether/maleic anhydride copolymers, ethyl cellulose, ethylhydroxyethyl cellulose, stearic acid, glyceryl monooleate, cetyl alcohol and calcium stearate.

7. A membrane coated hydrogel capsule as recited in claim 1 wherein the solvent is water.

8. A method for encapsulating meristematic tissue and separating the tissue from its environment comprising:
encapsulating meristematic tissue substantially free of intact seed coat in a hydrogel capsule; and
surrounding the capsule with at least one membrane which controls the migration of solvents and their included solutes between the capsules and its environment, thereby creating an analog to natural botanic seed having an artificial seed coat which provides the benefits of natural seed coat.

9. A method as recited in claim 8 further comprising encapsulating the meristematic tissue in a gel matrix comprising at least one agent selected from the group consisting of sodium alginate, guar gum, carrageenan with locust bean gum, sodium alginate with gelatin, carboxymethylcellulose, gum tragacanth, sodium pectate, vinyl acetate, Furcellaran, pectin, hypnean, dextran, tamarind, amylose, agar, agarose, agar with gelatin, starch, amylopectin, corhull gum, starch arabogalactan, gum ghatti, gum karagan, Ti gum, wheat gum, chitin, dextrin, ethyl succinylated cellulose, succinylated zein, methylcellulose, hydroxylethyl cellulose, gelatin with glutaraldehyde, polyacrylamide, polyethylene glycol, polyvinylpyrrolidone, polyoxyethylene, hydrophillic urethane, polyvinylacetate, vinyl resins, Hydron (hydroxyethylmethacrylate), 2-methyl-5-vinylpyridine-methylacrylate-metylacrylic acid, sodium polystyrene sulfonate with polyvinylmethylpyridinium chloride, sodium polystyrene sulfonate with polyvinylbenzyltrimethylammonium chloride, strongly acidic polyanions with strongly basic polycations, Bordon Poly Co. 2113 ® (vinyl acetate homopolymer), Gelvatol ® (polyvinyl alcohol resin), Super Slurper ®, Viterra ®, Laponite ®, Gelrite ®, SeaKem ®, SeaPlaque ®Seaprep ®, IsoGel ®, methylan clear wallpaper paste, lactose, wax, clay, fly ash feldspar, celrite, bentonite, vermiculite, diatomaceous earth, lime, calcium carbonate, calcium oxide, magnesium carbonate, sodium bicarbonate and urea.

10. A method as recited in claim 8 further comprising encapsulating the meristematic tissue in a hydrogel capsule and surrounding the capsule with at least one membrane compound selected from the group consisting of ethylene vinyl acetate acrylic acid terpolymers, ethylene vinyl acetate copolymers, spermaceti, aluminum starates, methyl vinyl ether/maleic anhydride copolymers, ethyl cellulose, ethylhydroxyethyl cellulose, stearic acid, glyceryl monooleate, cetyl alcohol, calcium stearate, methylvinyl ether/maleic anhydride, styrene maleic acid copolymer, styrene maleic anhydride copolymer, ethylene maleic acid copolymer, ethylcellulose, iospropyl myristate, polyvinyl acetate phthalate, starch acetate phthalate, amylose acetate phthalate, cellulose acetate phthalate, saran, butyl rubber, keratin, shellac, carnuba wax, paraffin wax, fats, lipids, triglycerides, benzyl cellulose and petrolatum.

11. A method as recited in claim 8 further comprising encapsulating the meristematic tissue in a hydrogel capsule and surrounding the capsule with at least one membrane compound selected from the group consisting of ethylene vinyl acetate acrylic acid terpolymers, ethylene vinyl acetate copolymers, spermaceti, aluminum stearates, methyl vinyl ether/maleic anhydride copolymers, ethyl cellulose, ethylhydroxyethyl cellulose, stearic acid, glyceryl monooleate, cetyl alcohol and calcium stearate.

12. A method as recited in claim 8 further comprising encapsulating the meristematic tissue in a hydrogel capsule comprising a gel matrix comprising at least one agent selected from the group consisting of sodium alginate, guar gum, carrageenan with locust bean gum, sodium alginate with gelatin, carboxymethylellulose, gum tragacanth, sodium pectate and vinyl acetate.

13. A method as recited in claim 8 further comprising:
encapsulating the meristematic tissue in a hydrogel capsule comprising a gel matrix comprising at least one agent selected from the group consisting of sodium alginate, guar gum, carrageenan with locust bean gum, sodium alginate with gelatin, carboxymethylcellulose, gum tragacanth, sodium pectate and vinyl acetate; and surrounding the capsule with at least one membrane compound selected from the group consisting of ethylene vinyl acetate acrylic acid terpolymers, ethylene vinyl acetate copolymers, spermaceti, aluminum starates, methyl vinyl ether/maleic anhydride copolymers, ethyl cellulose, ethylhydroxyethyl cellulose, stearic acid, glyceryl monooleate, cetyl alcohol and calcium stearate.

14. A method as recited in claim 8 wherein he solvent is water.

* * * * *

UNITED STATES PATENT AND TRADEMARK OFFICE
CERTIFICATE OF CORRECTION

PATENT NO. : 4,715,143

DATED : Dec. 29, 1987

INVENTOR(S) : M. Keith Redenbaugh and Zoila Reyes

It is certified that error appears in the above—identified patent and that said Letters Patent is hereby corrected as shown below:

Col. 1, line 12, "562,663" should be --4,562,663--.

Col. 2, line 50, "to" should be --of--.

Col. 3, line 52, should end with "(hydroxyethylmethacrylate)" and line 53 should begin with "2-methyl-5-...".

Col. 12, line 50, "starates" should be --stearates--.

Col. 14, line 8, "starates" should be --stearates--.

Col. 14, line 12 "he" should be --the--.

Signed and Sealed this

Twenty-fourth Day of May, 1988

Attest:

DONALD J. QUIGG

*Attesting Officer*         *Commissioner of Patents and Trademarks*